United States Patent [19]

Tsurumizu et al.

[11] Patent Number: 5,240,704
[45] Date of Patent: Aug. 31, 1993

[54] VACCINE, ANTIBODIES & ANTIBODY-CONTAINING COMPOSITIONS FOR INHIBITING HUMAN DENTAL CARIES INDUCED BY STREPTOCOCCUS MUTANS

[75] Inventors: Takashi Tsurumizu, Chiba; Takashi Hashimoto, Tokyo, both of Japan

[73] Assignee: Kitasato Kenkyusho, Tokyo, Japan

[21] Appl. No.: 902,528

[22] Filed: Jun. 22, 1992

Related U.S. Application Data

[63] Continuation of Ser. No. 511,869, Apr. 18, 1990, abandoned, which is a continuation of Ser. No. 185,300, Apr. 19, 1988, abandoned, which is a continuation of Ser. No. 876,326, Jun. 19, 1986, abandoned, which is a continuation-in-part of Ser. No. 634,654, Jul. 25, 1984, abandoned, which is a continuation-in-part of Ser. No. 535,183, Sep. 23, 1983, abandoned.

[30] Foreign Application Priority Data

Jul. 3, 1983 [JP] Japan ................................ 58-135451
Sep. 20, 1983 [JP] Japan ................................ 58-173618

[51] Int. Cl.$^5$ ..................... A61K 39/00; A61K 39/40; A61K 35/16
[52] U.S. Cl. ..................... 424/85.8; 424/87; 530/387.1
[58] Field of Search ...................... 424/85.8, 87, 93 H; 530/387.1

[56] References Cited

U.S. PATENT DOCUMENTS

| | | | |
|---|---|---|---|
| 3,879,545 | 4/1975 | Gaffar et al. | 424/92 |
| 4,150,116 | 4/1979 | Taubman et al. | 424/50 |
| 4,287,173 | 9/1981 | Carlo et al. | 424/49 |
| 4,324,782 | 4/1982 | Beck | 424/85 |
| 4,442,085 | 4/1984 | Colman | 424/92 |
| 4,521,513 | 6/1985 | Russell | 424/85 |

FOREIGN PATENT DOCUMENTS 1505513 5/1975 United Kingdom .

OTHER PUBLICATIONS

Scully et al Specificity of opsonizing antibodies to antigens of S. mutans. 1980 Immunology 41:467–73.
Davis et al Microbiology. 3rd ed p. 1269 1980.
Krause et al., Japanese Bacteriological Society, vol. 38, No. 1, Jan. 25, 1983.

Primary Examiner—Christine M. Nucker
Assistant Examiner—Hazel F. Sidberry
Attorney, Agent, or Firm—Schweitzer, Cornman & Gross

[57] ABSTRACT

PLS antigens I and II are derived from the pili-like structures on the cell wall of Human type Streptococcus mutans of the serotypes c, e, f and g and the serotype d, respectively and capable of specifically inhibiting the adherence (infection) of the corresponding strains to the teeth of humans. These antigens are a kind of glycoprotein comprising protein (about 15–25%) and carbohydrates (about 75–85%) and have a molecular weight of about 60,000–90,000. It is possible to isolate these antigen by extracting the intact cells in a hypertonic buffer solution at a pH of 6–8 and at a temperature below the denaturing point of the antigenic protein and fractionating the resultant antigen from the extract thereby obtained. A non-cariogenic vaccine comprises as antigen PLS antigens I and/or II. Non-cariogenic antibodies may be obtained by immunizing a mammal with PLS antigens I and/or II to produce the corresponding antibodies in the body of the mammal and recovering the resultant antibodies from the mammal. Non-cariogenic compositions comprises an effective amount of antibodies to PLS antigens I and/or II in association with a pharmaceutical carrier or excipient which may preferably suitable for oral administration. Preferred compositions are exemplified by dentifrices, gargles, ice creams, chewing gums, candies and the like.

8 Claims, 1 Drawing Sheet

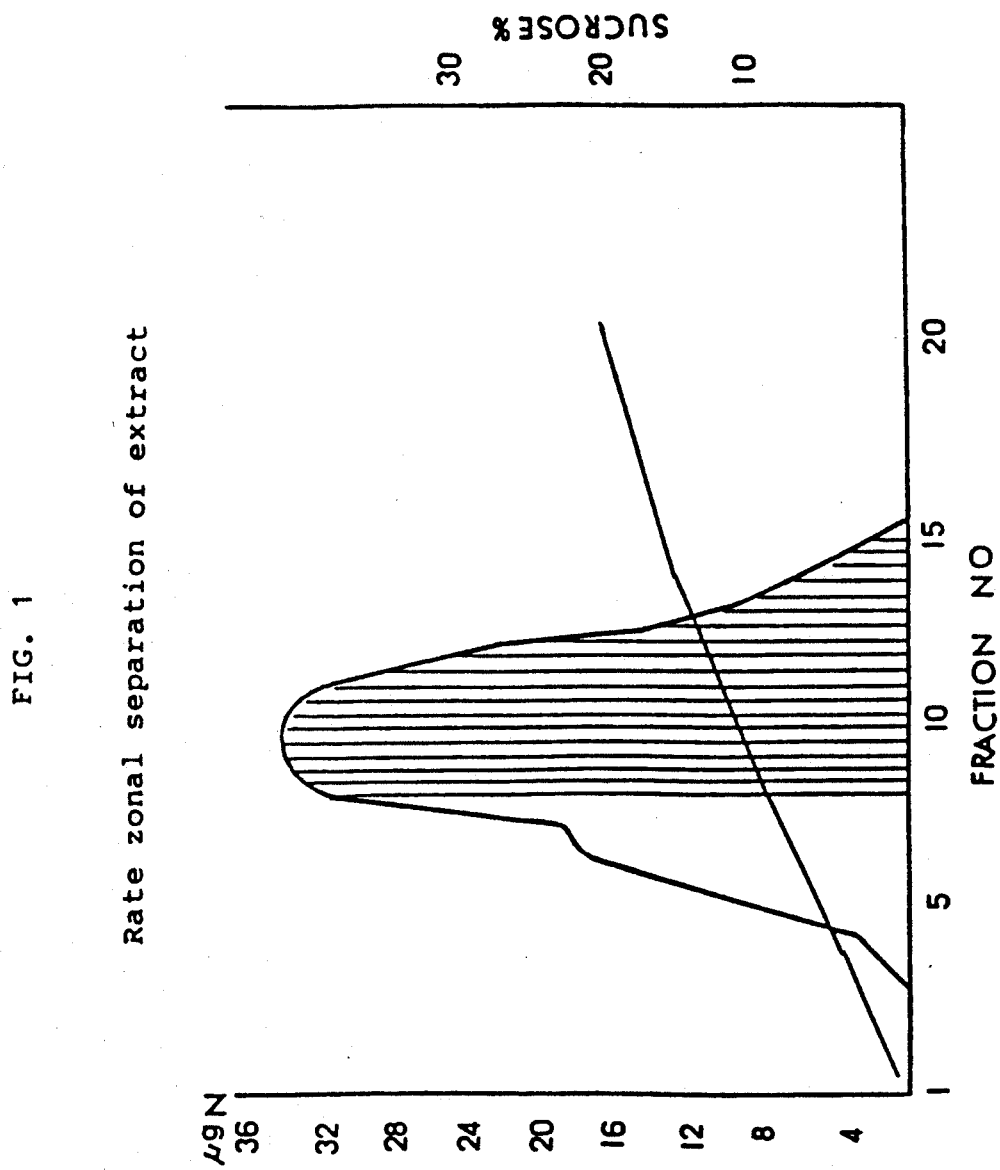
FIG. 1 Rate zonal separation of extract

VACCINE, ANTIBODIES & ANTIBODY-CONTAINING COMPOSITIONS FOR INHIBITING HUMAN DENTAL CARIES INDUCED BY STREPTOCOCCUS MUTANS

This is a continuing application of U.S. Ser. No. 511,869, filed on Apr. 18, 1990, which is a continuation application of U.S. Ser. No. 185,300, filed Apr. 19, 1988, which is a continuation of U.S. Ser. No. 876,326, filed Jun. 19, 1986, which is a continuation-in-part of U.S. Ser. No. 634,654, filed Jul. 25, 1984, which is a continuation-in-part of U.S. Ser. No. 535,183, filed Sep. 23, 1983, all now abandoned.

RELATED APPLICATIONS

The present application is a continuation-in-part of U.S. Patent application Ser. No. 634,654 filed on Jul. 25, 1984 now pending and which in turn is a continuation-in-part of U.S. Patent application Ser. No. 535,183 filed on Sep. 23, 1983, which is also now pending.

FIELD OF THE INVENTION

The present invention relates to vaccine, antibodies and antibody-containing compositions for preventing or inhibiting human dental caries induced by *Streptococcus mutans*.

BACKGROUND OF THE INVENTION

Dental caries is a disease of humans and animals, which is primarily induced on the surface of a tooth by the action of cariogenic oral bacilli and progressively breaks down its structure. Among various cariogenic oral bacilli, *Streptococcus mutans* is believed to be the most important. It has previously been reported, for example, in Bergy's Manual of Determinative Bacteriology, page 502 (1974) that a relationship exists between dental caries and S. mutans. It is suggested that *S. mutans* is a similar organism to *S. salivarius*, even though *S. mutans* has not yet been extensively studied and compared with *S. salivarius*. Nowadays, however, typical oral streptococci are clearly distinguished from each other, for example, with reference to the following characteristics:- (a) *S. mutans* decomposes mannitol and sorbitol and also produces both water-soluble and insoluble dextran-like polysaccharides (hereinafter referred to as DPS) from sucrose. (b) *S. sanguis* produces from sucrose water-soluble DPS having a weaker adhering ability and also produces ammonia from arginine; and (c) *S. salivarius* produces fructans from sucrose.

As is well known, insoluble DPS produced by *S. mutans* adhere to the surface of teeth to form dental plaque. The major portion of *S. mutans* in the oral floras resides in the plaque and produces lactic acid which is believed to break down the teeth. Other cariogenic oral bacilli also produce lactic acid. However, the lactic acid produced by *S. mutans* is not released from the plaque, but directly accumulates on the surface of the tooth.

Strains of *S. mutans* are classified according to the classification by Bratthal et al into 7 serological groups (serotypes), designated "a" to "g", in view of the immunological specificities of their cell wall antigens (Bratthal. Odont. Rev. 20:141, 1970 and ibid., 20:23, 1970 and Perch et al, Acta. Path. Microbiol. Scand. Section B, 82:357, 1974). A further classification scheme for classification of *S. mutans* has been proposed by Makoto Sato. According to this classification scheme, strains of *S. mutans* are classified into Human I (HI), Human II (HII) and Rat (R) types. The following has been reported by Sato:

93.9% of *S. mutans* of human origin were Human I type and the rest being Human II type;
(b) all strains of rat origin were Rat type;
(c) no *S. mutans* was isolated from mice and guinea pigs;
(d) all strains originating from hamsters and monkeys were Human I type;
(e) Human I, Human II and Rat types correspond to "c, e and f", "d and g", and "a and b" serotypes of Bratthal's classification (J. of Dental Health, Vol. 28, No. 2, pages 100–123 1978 in the Japanese version).

Possible approaches for inhibiting human dental caries induced by *S. mutans* by immunological means have previously been put forward. British Patent 1,375,866, for example, discloses a dental vaccine which comprises as antigen at least a part of the cell of a cariogenic strain of *S. mutans* SSC, of which characteristics are the same as the characteristics of *Streptococcus mutans* NCTC 10449 which is a well-recognized representative cariogenic strain present in the oral cavity of humans. This patent discloses as preferred antigens, the cell wall and the enzyme from the cultured broth. All vaccines described in its examples use, as antigen, the whole cells inactivated with formalin or phenol. However, it is well known that administration of whole cell antigen originating from *S. mutans* to animals is liable to cause various undesirable side effects such as, for example, cross-reaction with the heart muscle antigen, allergic reaction and the like. To our knowledge, it has not yet been reported that such a vaccine has been used to inhibit human dental caries induced by *S. mutans* with good results.

British Patent No. 1,505,513 and U.S. Pat. No. 4,324,784 disclose cow's milk containing antibodies for inhibiting *S. mutans*, produced by immunizing a cow with heat-inactivated whole cells of particular strains of *S. mutans* viz. *S. mutans* AHT, BHT, 10449 and 6715 respectively of the serotypes of "a", "b", "c" and "d". However, the known cow's milk cannot be considered suitable for human use, since the cow's milk lacks antibodies capable of inhibiting *S. mutans* 10449 (serotype "c"; Human I type) which is well recognized as a representative cariogenic strain in the oral cavity of humans or any other strains of Human I type *S. mutans*, which represents more than 90% of cariogenic strains in the oral cavity of humans, even though the cow's milk is more or less active upon *S. mutans* 6715 (serotype "d").

U.S. Pat. No. 4,442,085 (Colman) discloses that Antigen A capable of inhibiting *S. mutans* and having a molecular weight of 32,000–26,000 and an isoelectric point of 4.3 is present in the cell walls and cultures of strains of *S. mutans* of serotypes "c, e and f". Antigen A may be extracted from the cell wall by a boiling aqueous solution of SDS(sodium dodecyl sulfate); a detergent followed by chromatography of the resultant precipitate for purification. However, it is not clear whether Antigen A is active upon Human II type strains (serotypes "d and g").

U.S. Pat. No. 4,521,513 (Russell) discloses that Antigen C capable of inhibiting *S. mutans* and having a molecular weight of 65,000–75,000 and an isoelectric point of 4.21 to 4.69 is present in the cell walls and cultures of strains of *S. mutans* of serotypes "c, e and f". Antigen C may be separated from the cell extract with a boiling solution of sodium dodecyl sulphate (detergent) and purified by chromatography., or from the culture filtrate and cell extract by chromatography.

However, it is not clear whether Antigen C is active upon Human II type strains of S. mutans.

U.S. Pat. No. 4,150,116 (Taubman et al) discloses that purified glucosyltransferase (GFT) is capable of inhibiting S. mutans, which may be recovered from cellular polysaccharide with a denaturing agent and purified by chromatography.

Bowen et al (British Dent. J. Vol. 139, pp. 45–58, 1975) disclose that various antigens originating from strains of S. mutans such as antigens from the whole cells, broken cells and glucosyltransferase etc. may be used for immunizing animals preferably by intramucosal injection.

Meanwhile, it was previously known that strains of S. mutans have the pili-like structures (fimbriae) on the surface of the cell wall, by means of which they adhere (infect) to the oral cavity of humans and animals (Gibbons et al, Ann. Rev. Microbiol., 29:19–44, 1975). However, it has not yet been reported in the art that antigen originating from such pili-like structures of S. mutans is capable of specifically inhibiting or preventing the adherence (infection) of strains of S. mutans to the oral cavity of humans.

The present invention is based upon the discovery that antigens which we have isolated from the pili-like structures (PLS) of strains of Human type S. mutans are capable of inhibiting the adherence (infection) of strains of Human type S. mutans to the oral cavity of humans with excellent results and that the desired antigens may be extracted by using a hypertonic buffer solution under mild conditions.

SUMMARY OF THE INVENTION

The present invention is directed to provide a process for producing an antigen preparation for inhibiting or preventing human dental caries induced by Streptococcus mutans, a vaccine containing such antigen or antigens, a process for producing antibodies for inhibiting or preventing human dental caries induced by S. mutans and anti-dental caries compositions containing such antibodies.

According to one feature of the present invention, there is provided a process for isolating at least one antigen selected from the two antigens for preventing or inhibiting human dental caries induced by Streptococcus mutans, comprising separating the whole cells of at least one strain of Streptococcus mutans from the cultured broth thereof, extracting at least one antigen from the pili-like structures (PLS) on the surface of said whole cells in a hypertonic solution at a pH of from 6 to 8 and at a temperature below the denaturing temperature of said at least one antigen and fractionating the resultant antigen from the extract thereby obtained, said at least one strain being selected from the two strain types of S. mutnas mutans, the first of which is selected from strains of serotypes "c, e, f and g" and the second of which is selected from strains of serotype "d".

A vaccine for inhibiting or preventing human dental caries induced by S. mutans, comprises an effective amount of at least one of said two PLS antigens in association with a pharmaceutically acceptable carrier.

By immunizing a mammal with at least one PLS antigen to produce the corresponding antibodies in the body of said mammal and recovering the resultant antibodies from said mammal, it is possible to obtain antibodies for inhibiting or preventing human dental caries induced by S. mutans.

Compositions for inhibiting or preventing human dental caries induced by S. mutans provided by the present invention, comprise an effective amount of antibodies to PLS antigen I and/or antibodies to PLS antigen I, in association with a pharmaceutically acceptable carrier or excipient.

DESCRIPTION OF THE INVENTION

In our experiments, PLS antigen isolated from Streptococcus mutans NCTC 10449, which is well-recognized as a representative strain of S. mutans found in the oral cavity of humans (serotype c; Human I type) was subjected to quantitative determination of protein (by Hartree's method, using bovine serum albumin as reference) and carbohydrates (by the phenol/sulfuric acid method, using D-glucose as reference), and its molecular weight was determined by gel filtration using Sephadex G-100 (Pharmacia Fine Chemicals AB., Sweden)-with reference to phosphorylase b, bovine serum albumin, egg albumin, chymotrypsinogen and the like having known molecular weights. Similar studies were also performed using certain strains of S. mutans which are well-recognized reference strains such as S. mutans Ingbritt (serotype c), OMZ176 (serotype d), P4 (serotype e), OMZ175 (serotype f) and K1R (serotype e). The results are as follows:

(1) A PLS antigen is an acidic protein containing about 15–25% (e.g. about 20%) protein and about 75–85% (e.g. about 80%) carbohydrates and having a molecular weight of about 60,000–90,000 (e.g. ca. 75,000).

(2) Polyacrylamide disc electrophoresis of a PLS antigen results in a characteristics broad band towards the cathode.

(3) If sucrose density-gradient ultracentrifugation is carried out with a PLS antigen, the antigen is found in the fractions having a sucrose density of about 10–20% and a specific gravity of about 1.3 to 1.4.

(4) If gel filtration of a PLS antigen is carried out using Sephadex G-100 (Pharmacia Fine Chemicals AB., Sweden), two peaks are eluted (monitored by absorption at 280 nm). The PLS antigen is recovered from the first peak, of which reactivity with human or rabbit serum is positive.

(5) A PI value for a PLS antigen of not more than about 3.5 may be obtained by the electric focusing method according to Versterberg et al method using 1% of the carrier ampholite (pH 3.0–10.0; commercial product of LKB Produkter AB., Sweden).

The above-mentioned physical characteristics indicate that the PLS antigens of the present invention are clearly distinguishable from the known antigens originating from S. mutans.

It has been found that no significant difference between the fractionating patterns of the PLS antigens originating from all Human type strains of S. mutans, although the serological characteristics of the PLS antigens of S. mutans are not identical with each other and may be classified into 3 types viz. "a and b", "c, e, f and g" and "d" according to the serotypes of the origins.

The term "PLS antigen" used herein denotes an antigen isolated from the pili-like structures on the surface layer of the cell wall of S. mutans. The fact is that certain oral bacteria have such pili-like structures (fimbriae). However, the known antigen preparations comprising antigens originating from the whole cells, broken cells, cell walls, cell cultures and the like of such oral bacteria do not show or recognize that such PLS antigens are capable of specifically inhibiting the adherence (infection) of the microorganism to the tissues in the oral cavity of the hosts.

The PLS antigen of the present invention may be obtained in the following manner.

Any and all strains of Human type *S. mutans* may be used for the purpose of the present invention, although the use of strains having stronger cariogenic potentials is preferred. The desired strains may easily be selected, for example, with reference to higher ability to adhere to the tube wall. Both wild strains and mutant strains of Human type *S. mutans* may be used for the purpose of the present invention so far as they exhibit strong adhering ability.

DRAWING

FIG. 1 shows the fractionation pattern obtained by the sucrose-density gradient ultracentrifugation described in Example 3.

In the examples and experiments described hereinafter, *Streptococcus mutans* Mutant Strain K-Dp (FERM BP-317; serotype "c") and Streptocuccus mutans Strain KH2 (FERM BP-366; serotype "d") are used, which are induced from the corresponding wild strains of *S. mutans* of human origin. These mutant strains are characterized by their strong ability to adhere (infect), and other characteristics are substantially the same as the corresponding characteristics of their parent strains. These strains have been filed with Bikoken (The Fermentation Research Institute) of The Japanese Government respectively on Mar. 5, 1982 and Jul. 23, 1983 on the basis of The Budapest Treaty.

The mutant strains which may be used for the purpose of the present invention may be obtained, for example, in the following manner. Wild strains of Human type *S. mutans* are treated in the conventional manner, for example, by using a suitable mutagen such as nitrogen mustard, nitrosoguanidine, irradiation by ultraviolet rays and the like. The desired strains are selected with respect to stronger adhering ability. The selected strains are collected and cultured purely. If desired, the same procedure may be repeated until a desired strain is obtained. It has been found that the resultant mutant strains are genetically stable.

Both wild strains and mutant strains of Human type *S. mutans* will serve. Preferred strains may easily be selected, for example, with reference to their stronger ability to adhere to the tube wall.

Culturing of the strains which may be used for the purpose of the present invention may be effected in conventional manner Thus, culturing may be effected under anaerobic conditions, although aerobic culturing may be possible, if desired. The use of liquid media is preferred for mass propagation, although both synthetic and organic media may be used. In practice, culturing may be effected, for example, at a pH of 5.6 to 8.0 (for example, about 7.0) and at a temperature of from 23°-39° C. (for example, about 37° C.) for 24 to 72 hours (for example, 48 hours). Various known media for culturing streptococci may be used for the purpose of the present invention. Preferred media include Medium A having the following composition:

Medium A (%): polypeptone 1.7; polypeptone S (Difco., U.S.A.) 0.3; yeast extract 0.5; potassium phosphate, dibasic 0.25; sodium chloride 0.5; glucose 0.25 (pH=7.0 to 7.8)

After completion of culturing, the cells are separated from the cultured broth, for example, by centrifugation (e.g. 8000 r.p.m/20 in.). The separated cells are suspended in a suitable buffer solution conventionally used for isolation of antigens from intact cells, such as, for example, 0.1–1M acetic acid/sodium acetate buffer solution (pH 6.0–7.8) and 0.01–0.75M phosphate buffer solution which contains about 0.8–1.2M sodium chloride to exert a high osmotic pressure upon the cells. The cell suspension may, if desired also contain a suitable surfactant such as, for example, Triton X-100 (Rohm and Haas Co., U.S.A.). The cell suspension may, if desired, be treated with ultrasonic waves (e.g. 10–20 KHz/5–20 min). Electron microscopic observation has indicated that by the osmotic action of the hypertonic solution, it is possible to isolate the desired PLS antigen effectively. Although we do not wish to be bound with theoretical consideration, it is believed that owing to high osmotic pressure, the semipermeability of the cell wall is decreased and, as a result, the pili-like structures (fimbriae) are separated from the cell wall.

The resultant extracted solution containing the desired PLS antigen may be fractionated and purified in conventional manner, for example, by the sole or combined use of column chromatography, isoelectric focusing precipitation, fractional precipitation using a cold solvent such as ethanol, salting-out using ammonium sulfate and the like. Especially good results may be obtained by rate zonal ultracentrifugation such as sucrose density-gradient ultracentrifugation.

If desired, it is also possible to add to the cultured broth ammonium sulfate to about 20–70% (e.g. 33%), followed by agitation to dissolve the ammonium sulfate. The mixture is allowed to stand at a low temperature (for example, 4° C.) for 24–48 hours to form a precipitate containing the desired antigen. After removal of the supernatant, the precipitated fraction is collected and densely suspended in a similar buffer solution (pH about 6–8) and dialyzed against a similar buffer solution at a low temperature (for example, 4° C.) to remove the ammonium sulfate and any dialyzeable impurities. The residual solution is collected and centrifuged (e.g. 8000 r.p.m./20 min) to obtain an extracted solution containing the PLS antigen.

It is known that antigenic protein may be denatured at around 60° C. In order to avoid denaturation of the PLS antigen, the extraction, fractionation and purification of the antigen may be effected at a temperature below the denaturing temperature, for example, at a temperature below the room temperature (for example, below 10° C.).

The purified PLS antigen solution may, if desired, be treated with a suitable inactivating agent such as, for example, formalin (0.2–0.02%). This is followed by dialysis against a similar buffer solution to remove the inactivating agent in a conventional manner. The use of phenol does not give good results.

The antigen solution is then diluted, for example, with 0.5–1M phosphate-buffered 0.5–1M sodium chloride solution (pH 6–8) to adjust the protein N concentration, for example, to 5–50 mcg/ml. To this solution aluminium hydroxide gel is added at a final concentration of aluminium of about 40–200 mcg/ml to adsorb the antigen. If desired, a suitable antiseptic agent such as, for example, thimerosal (0.05–0.1 % w/v) may be added. The resultant PLS antigen solution, in association with a pharmaceutically acceptable carrier, may be used as the vaccine of the present invention.

The vaccine of the present invention may be administered to humans by injection under the skin or into the muscle (for example, under the mucous membrane in the oral cavity), for example, in an amount of 0.2 to 2.0 ml/injection. The administration may be effected, for example, 2 to 5 times at an interval of 2 to 5 weeks. It is also possible, if desired, to administer the vaccine daily, for example, for 3 to 12 days continuously.

It has been observed that by administration of the vaccine of the present invention, it is possible to inhibit adherence (infection) of the wild strains of *S. mutans* to the teeth. However, the growth of the wild strains themselves and accordingly the production of the metabolized products such as DPS may not be inhibited. The formation of agglutinin has not been observed. The inhibited strains of *S. mutans* are massively coagulated, for example, in the saliva, from which they may easily be removed in conventional manner, for example, by using usual dental pastes rinses and gargles.

As a result of various tests using hamsters and humans, it has been found that the wild strains of *S. mutans* disappeared from the oral floras by administering the vaccine of the present invention, for example, 2 to 4 times. In the case of hamsters, to which a large amount of a dental vaccine of the present invention was continuously administered over an extended period of time, for example, for 6 to 12 months, no unusual occurrence was noted upon the pathogenic examination of the animals.

In order to investigate the adherence-inhibiting abilities of the various PLS antigens of different origins, sample vaccines were prepared using the PLS antigens originating from the strains of Human type S. mutans (serotypes "c" to "g") respectively.

By administering each sample to hamsters, the following immunological effects have been noted:(a)

(a) The PLS antigens originating from strains of S. mutans of the serotypes "c, e, f and g" (hereinafter referred to as PLS antigen I) may indifferently inhibit the adhering ability of the wild strains of *S. mutans* of these serotypes.
(b) It is possible to inhibit the wild strains of *S. mutans* of the serotype "d" by the sole use of PLS antigen I. But the inhibiting ability of PLS antigen I against the strains of the serotype "d" is likely to be weaker than that against the strains of the serotypes "c, e, f and g".
(c) PLS-antigen II viz. the antigen originating from the strains of the serotype "d" is capable of specifically inhibiting the strains of the serotype "d". Its inhibiting ability against the strains of the serotypes other than "d" type is significantly weaker than its inhibiting activity against strains of serotype "d".

The above-mentioned findings clearly indicate that the combined use of PLS antigens I and II is preferred for practical purpose, even though the sole use of either PLS antigen I or II is capable of inhibiting all Human type strains of *S. mutans*.

The antibodies for inhibiting dental caries induced by cariogenic strains of *S. mutans* may be produced by the process of the present invention, which comprises administering at least one vaccine or PLS antigen solution, as defined above, to a mammal to produce antibodies in its body and recovering the resultant antibodies from the mammal.

The PLS antigen solution which may be used for immunizing a mammal may be prepared in a similar manner to that described above. However, it is preferred to adjust the concentration of protein N and the final concentration of aluminium, for example, to 10-200 (for example, about 50) mcg/ml ant 5-2000 (for example, 500-1000 mcg/ml) respectively. If desired, an equal amount of Fruend's complete adjuvant may be used instead of aluminium hydroxide gel.

The immunization may be effected in a conventional manner, for example, by injection. As mammals, smaller mammals such as, for example, mice, rats and guinea pigs or larger mammals such as, for example, rabbits, goats, sheep, horses and cattle may be used.

The dose of the PLS antigen may vary, depending upon the type of the mammal. However, it is usually possible to administer the antigen solution to smaller animals at a dose of 100-2000 mcg (once daily on the basis of protein N) by injection, for example, under the skin on the back of the mammal. The immunization may be effected, for example, 2-5 times with an interval of 2-5 weeks. If desired, the immunization may be effected by oral administration, for example, at a 5-10 fold greater dose and may be continued, for example, 3-12 days. For example, in the case of a rabbit, a PLS antigen solution containing about 100-200 mcg of protein N may be mixed, for example, with an equal amount of Freund's complete adjuvant and injected under the skin on the back of the animal once daily for 2-5 times with an interval of 2-5 weeks. In the case of a larger animals such as, for example, horses, it is possible to administer, for example, a same amount of the PLS antigen preparation as used for rabbit. In this case, however, the administration may be continued over a larger period of time, for example, for one year.

For example, 10-14 days after the final immunization, blood is collected from the animal in conventional manner and is used for the preparation of a plasma which may, if desired, by further purified to obtain an antiserum. The resultant plasma or antiserum may be freeze-dried and preserved over an extended period of time and may be administered to humans without further processing.

If desired, it is possible to immunize a mammal with PLS antigens I and II in combination, although it is preferred to use either PLS antigen I or II alone.

The compositions of the present invention for inhibiting human dental caries induced by cariogenic strains of *S. mutans* comprises as active ingredient an effective amount of PLS antigen I antibodies and/or PLS antigen II antibodies. However, for the reason as set forth above, the combined use of two antibodies is preferred.

The carriers or excipients which may be used in the preparation of the compositions of the present invention may be solid, semi-solid or liquid and thus the compositions will generally be solid, semi-solid or liquid compositions suitable for oral administration. Thus, the compositions may take the forms of powders, capsules, granules, tablets, drops, suspensions, emulsions and the like. Examples of suitable solid carriers include lactose, potato- or soluble starch, magnesium stearate, clay and kieselguhr. Suitable liquid carriers are exemplified by water, saline solution, glycerol, almond oil, yogurt and juice. The compositions may further contain, if desired, bonding agents, stabilizers, emulsifiers, dispersants, essence and various other additives conventionally used in the art. Preferred examples of the compositions of the present invention include, for example, dentifrices, gargles, candies, chewing gums, ice creams and the like.

In order to administer a given amount of antibodies of the present invention to humans simply and effectively, the compositions may be formulated, for example, in the forms of tablets, capsules, ampoules, bacdals, troches and the like. The amount of antibodies contained in such a dosage unit form may vary, depending upon the types of the dosage unit forms and the purpose of administration. In one embodiment, such a dosage unit form contains antibodies of the present invention in such an amount that it is enough to administer 1-10 units as hereinafter defined, of the antibodies once daily. Various test using humans and hamsters have revealed that strains of S. mutans may be removed from the oral cavity of humans by, for example, by administration for several weeks of antibodies raised against at least one PLS antigen at a daily dose of 1-4 units (as hereinafter defined).

Over an extended period of time, for example, 6-12 months, a large amount of antibodies of the present invention were continuously administered to the oral cavity of hamsters. After this, all these animals were pathogenically examined and found to be normal.

In this specification, the unit of the antibody titre is expressed by the precipitation value obtained by the double diffusion method with reference to Goldman et al (Isolation and Characterization of Glial Filaments from Human Brain, J. Cell. Biol., 78:426, 1978).

In the following non-limiting examples and experiments which illustrate the invention, culturing was effected at 37° C. under aerobic conditions using commercially available media at their specified pHs, unless otherwise specified.

EXAMPLE 1

Preparation of Streptococcus mutans Mutant Strain K-Dp (FERM BP 317):

Fresh wild strains of S. mutans (serotype "c") were isolated from the oral cavity of a human and cultured for 24 hours by using Dott Heuwitt Broth (20 ml;37° C.; commercial product of Baltimore Laboratories, Inc., U.S.A., hereinafter referred to as BBL.). After completion of culturing, the cells were separated from the cultured broth by centrifugation (8000 r.p.m./20 min) and then washed 3 times with 100 ml of 0.75M phosphate-buffered 1M sodium chloride solution (pH 6.8) by centrifugation (8000 r.p.m./20 min). The cells were suspended in a similar buffer solution (20 ml) containing 20% nitrogen mustard at a concentration of about 10 living cells/ml and were kept at 37° C. until more than 90% of the cells were killed (for about 60-90 min.). The cells which survived were collected and cultured in a similar manner to that described above by using Dott Heuwitt Broth. After completion of culturing, one platinum loop of the cultured broth was transferred to TYC agar plate medium (Stoppellar et al, Archs Oral Biol., 12:1190-1201, 1976) for culturing for 24 hours. The cultured broth was allowed to stand at ambient temperature for 24 hours in order to select colonies capable of producing a large amount of insoluble DPS. If desired, the above-mentioned procedure may be repeated until a desired strain having a high capacity for producing insoluble DPS is obtained. The resultant strain was designated as Streptococcus mutans Mutant Strain K-Dp.

This mutant strain was orally administered to hamsters over an extended period of time or subcultured over more than 100 generations by using various known media to confirm that this strain exhibits a very high adhering ability and its characteristics are genetically stable.

EXAMPLE 2

Preparation of Streptococcus mutans Strain KH2 (FERM BP 366):

Fresh wild strains of S. mutans (serotype "d") were isolated from the oral cavity of a human and treated in a similar manner to that described in Example 1 to prepare a mutant strain having a very high adhering ability and genetically stable characteristics. The resultant mutant strain was designated as Streptococcus mutans Strain KH2.

EXAMPLE 3

Preparation of vaccine (PLS antigen I):

A seed medium (500 ml) and a main medium (15000 ml), both having the composition of Medium A as set forth, were used for culturing Streptococcus mutans Mutant Strain K-Dp (FERM BP 317) for 24 hours for each.

After completion of the fermentation, ammonium sulfate was added to the cultured broth to a concentration of 33% saturation. The mixture was stirred to dissolve ammonium sulfate and was then allowed to stand at 4° C. for 24 hours. After removal of the supernatant, the remaining fraction was centrifuged (8000 r.p.m./ 30 min) to recover the precipitate. The precipitate was suspended in a 0.1M phosphate-buffered 1M sodium chloride solution (pH 8.0; 750 ml) and stirred at 4° C. for 72 hours with rotation (1–5 r.p.m.). The cell suspension was centrifuged (8000 r.p.m./30 min) to remove the cells. Ammonium sulfate was added to the supernatant to a concentration of 60% saturation, followed by agitation to dissolve ammonium sulfate. The solution was allowed to stand at 4° C. for 48 hours to give a precipitate containing the desired PLS antigen. After removal of the supernatant, the precipitated fraction was centrifuged (8000 r.p.m./30 min). The resultant material was suspended in a similar buffer solution of sodium chloride (100 ml). The cell suspension was put in a cellophane tube and dialyzed at 4° C. for more than 48 hours against a similar buffer solution (more than 5000 ml) to remove the ammonium sulfate. The residual solution was centrifuged (8000 r.p.m./30 min) to remove dialyzeable impurities. The supernatant was recovered, of which 300 ml was diluted with a similar buffer solution of sodium chloride to give a protein N concentration of 200 mcg/ml. The diluted solution (200 ml) was subjected to sucrose density-gradient ultracentrifugation using Hitachi 65P Ultracentrifuge with a zonal rotor RP235T (commercial product of Hitachi Limited., Tokyo; sucrose density 30 %; 35000 r.p.m/18 hours). The desired PLS antigen was present in Fraction Nos. 8-15 having a specific gravity of about 1.31-1.35 and a sucrose density of about 10-12%. The resultant antigen solution contained 78 mcg/ml of protein N, which was diluted with a 0.75M phosphatebuffered 1M sodium chloride solution (pH 6.2-6.5) to a final concentration of protein N of 10-20 mcg/ml. To the diluted solution, aluminium hydroxide gel was added to a final concentration of aluminium of 500 mcg/ml, followed by addition of thimerosal (0.01 % w/v) as antiseptic agent. The resultant vaccine was designated as vaccine I.

EXAMPLE 4

Preparation of vaccine (PLS antigen) II:

Streptococcus mutans Strain KH2 (FERM BP 366; serotype "d") was treated in a similar manner to that described in Example 3 to obtain an antigen solution containing 125 mcg/ml of protein N, designated as antigen solution II, from which a vaccine, designated as vaccine II was prepared in a similar manner to that described in Example 3.

EXAMPLE 5

Preparation of vaccine (combination of PLS antigens I and II):

Antigen solutions I and II were respectively prepared by the methods of Examples 3 and 4 and combined together at the same concentration of protein N (10 mcg/ml) to obtain a mixed vaccine.

EXAMPLE 6

Preparation of PLS antigen I antibodies:

*S. mutans* Mutant Strain K-Dp (FERM BP 317) was cultured by using a seed medium (500 ml) containing polypeptone (1.7%; Wako Junyaku K.K., Japan), polypeptone S (0.3%; Wako Junyaku K.K., Japan), yeast extract (0.5%; Difco., U.S.A.), potassium phosphate, dibasic (0.25%), sodium chloride (0.25%) and glucose (0.25%) and having a pH of 7.0-7.8. After completion of culturing, the culture was transferred to the main medium (15000 ml) having the same composition as the seed medium for culturing 24 hours under the same conditions. After completion of culturing, ammonium sulfate was added to the cultured broth at a saturation of 33% and dissolved by agitation. The mixture was allowed to stand at room temperature for 24 hours. The supernatant was removed from the mixture. The precipitated fraction was recovered by centrifugation (8000 r.p.m./30 min) and suspended in 0.1 M phosphate-buffered 1 M sodium chloride solution (750 ml; pH 8.0). The cell suspension was allowed to stand at 4° C. for 72 hours, while stirring gently with 1-5 rotations/min. The suspension was centrifuged (8000 r.p.m./30 min) to remove the cells. Ammonium sulfate was added to the supernatant at a saturation of 60%. Ammonium sulfate was dissolved by agitation and the mixture was allowed to stand at 4° C. for 48 hours to form a precipitate containing the desired antigen. The supernatant was removed from the mixture and the precipitated fraction was recovered by centrifugation (8000 r.p.m./ 30 min). The recovered material was suspended in a similar phosphate-buffered sodium chloride solution to that described above (100 ml) and the resultant suspension was put into a cellophane tube for dialysis at 4° C. for more than 48 hours against a similar buffer solution (more than 5000 ml) to remove the ammonium sulfate and an dialyzeable impurities. The residual solution was centrifuged (8000 r.p.m./30 min) and the resultant supernatant was collected.

The supernatant (300 ml) was diluted with a similar phosphate-buffered sodium chloride solution at a protein N concentration of 100 mcg/ml. The diluted solution (200 ml) was subjected to sucrose density-gradient ultracentrifugation (sucrose density 5-30 %; 35000 r.p.m./18 hours) using a 65P Ultracentrifuge with a zonal rotor 235T (commercial product of Hitachi Limited, Tokyo).

The desired antigen was found in the fractions having a sucrose density of about 10-13% and a specific gravity of about 1.31-1.35, the amount of protein N of the desired PLS antigen being about 33-37 mcg/ml. The resultant extracted solution containing the desired antigen was put into a cellophane tube and concentrated to reduce the amount to 1/10 by using polyvinylpyrrolidone. The concentrated solution was then diluted with 0.75M phosphate-buffered 1M sodium chloride solution (pH 6.2-6.5) to a concentration of protein N of 50-100 mcg/ml. To the diluted solution was added an equal amount of Freund's complete adjuvant to obtain an antigen solution suitable for immunizing a mammal.

The resultant solution containing PLS antigen I (1.0 ml) was injected under the skin on the back of a rabbit having a body weight of about 3 kg in conventional manner. A similar immunization was effected 3 times in total with an interval of 4 weeks. 4 weeks after the final immunization, the animal was sacrificed by cardic puncture. Blood was collected from the animal, to which ammonium sulfate was added at a saturation of 33%. The blood was agitated to dissolve ammonium sulfate and then allowed to stand at 4° C. for 48 hours. The precipitate was collected by centrifugation (8000 r.p.m./20 min) and put into a cellophane tube for dialysis which was effected at 4° C. against purified water to remove the ammonium sulfate completely. The resultant solution was collected, concentrated and freeze-dried to obtain a PLS antigen I solution (about 85 ml).

EXAMPLE 7

Preparation of PLS antigen II antibodies:

In a similar manner to that described in Example 3, *Streptococcus mutans* KH2 (FERM BP 366; serotype "d") was cultured and treated to obtain an antibody-containing solution (about 85 ml).

EXAMPLE 8

A buccal was prepared in conventional manner by using glucose (1 g), antibody-containing solution (0.05 ml; PLS antigen I antibodies or PLS antigen II antibodies or a combination of such antibodies at an optional ratio) and soluble starch (0.05 g).

EXAMPLE 9

A syrup was prepared in conventional manner by using carboxymethyl-cellulose (CMM-Na; 0.2 g), 20 % fructose solution (20 ml), ethyl paraffine (0.04 g) and antibody-containing solution (0.1 ml; PLS antibodies I or PLS antigen II antibodies or a combination of such antibodies at an optional ratio).

EXAMPLE 10

A dental paste was prepared by mixing uniformly together calcium hydrogen phosphate (fine powder; 60%), glycerol (30%), CMC-Na (10%) and parabens (antiseptic agent; 0.25%) and adding to the mixture antibodies (PLS antigen I antibodies and/or PLS antigen II antibodies), such that the antibody titre was 2 units (as hereinbefore defined) per 50 ml of the product.

EXAMPLE 11

A non-cariogenic drink containing lactic acid-producing bacilli was prepared in the following manner. Skimmed milk (2000 ml) containing 10 % of solids was sterilized at 110° C. for 15 minutes, to which was then added *Lactobacillus casei* for culturing at 35°-37° C. for 36 hours. To the cultured broth was added 10% fructose 10 solution in order to adjust the concentration of *L. casei* to about $10^8$ living cells/ml. Antibodies raised against PLS antigens I and II were added to this solution and the titres of PLS antigen I antibodies and PLS antigen II antibodies were both adjusted to 4 units (as hereinbefore defined) per 50 ml of the resultant product.

EXAMPLE 12

Chewing gum:

Gum base (20%) was melt at 90° C. Corn syrup (25%) and lecithin (0.2%) were added to gum base and well mixed at 80° C. for 5 minutes. Fructose (55%) and citric acid (0.1%) were added to the mixture and cooled to 60° C. The mixture was well kneaded and added with antibodies to PLS antigens I and II (each 16 units per 100% of the material), followed by treating in conventionally manner to obtain a chewing gum.

Tests of the vaccines

Each of the vaccines respectively prepared by the methods of Examples 3, 4 and 5 was subjected to the dyeing test, the bacterial culturing test and the acute, abnormal toxity test, all being effected according to "Test Methods for General Test Standard for Biological Medicines (1979)" issued by The Ministry of Welfare, The Japanese Government in the following manner. Nothing unusual was noted.

(1) Dyeing test:

A sample vaccine (about 10 ml) was put in a test tube and centrifuged (about 2000 G/30 min) to form a precipitate. The precipitate was collected and smeared on a slide glass. Then, Gram's method was applied to the sample for dyeing test. The sample was observed microscopically (X 1000). No microorganism was noted.

(2) Bacterial negative test:

A sample vaccine (0.2 ml) was divided into two equal portions. Each fraction was cultured for 10 days at 30°-32° C. using thioglycolic acid medium (commercial product of BBL., U.S.A.). Nothing unusual was noted on the 2nd, 3rd, 6th, 7th and 10th days after the beginning of culturing.

(3) Abnormal acute toxicity negative test:

Five mice of 21 days old were abdominally injected with a sample vaccine (each 0.5 ml). Each animal was observed for subsequent 7 days. No unusual toxicity was noted.

Experiments

In the following experiments, Golden hamsters were used as test animals to investigate the inhibition of adherence of cariogenic $S.$ $mutans$ by using the vaccines and antibodies of the present invention. The animals were bred with a cariogenic diet (Diet 2000; commercial product of Funabashi Nojo, Japan) and deionized water ad libitum. Each group consisting of 10 females was used for the vaccines and each group consisted of 5 animals (male and female) for the antibodies unless otherwise specified.

Experiment 1

Vaccines (PLS antigens):

Immunological activities of vaccine I (PLS antigen I), vaccine II (PLS antigen II) and vaccine III (mixture of PLS antigens I and II disclosed in Example 5) were investigated in the following manner. (1) On each of the 18th and 25th days after birth, vaccine I, II or III (mixture of I and II) (0.2 ml/once daily) was injected under the skin of the baccal cavity of each animal of the test groups.

The cultured broths of $Streptococcus$ $mutans$ Mutant Strain K-Dp (FERM BP 317; serotype "c") and $Streptococcus$ $mutans$ Strain KH2 (FERM BP 366; serotype "d") respectively obtained by the methods of Examples 1 and 2 were centrifuged (each 8000 r.p.m./30 min) to separate the cells of two strains. The cells were suspended in a 0.75M phosphate-buffered 1M sodium chloride solution (pH about 6.5) at a concentration of about $10^6$ cells/ml for each strain. 0.1 ml of the resultant cell suspension was continuously administered to all animals between the 30th and 35th days after birth. The adherence of the strains of $S.$ $mutans$ to the teeth of all the animals was confirmed.

60 days after completion of administration of the vaccine, all animals were anesthetized with pentabarbital and abdominally injected with pilocarpin HCl (0.75 %; each 0.1 ml/100 g of body weight). The saliva was collected from each animal which was then killed by cardic puncture. The maxilla was removed from each animal and treated in an autoclave at about 120° C. for 1-2 minutes to remove the soft part. The remaining part was washed well with water and dried to obtain a sample of teeth.

The control animals were treated in a similar manner to that applied to the test animals without administering the vaccine.

(2) The infection ratio per the number of the animals of each group and the infection ratio per the number of molars were evaluated to investigate the induction of dental caries occurring in the test animals and control animals.

(3) In order to investigate the relationship of the antibodies present in the test animals with the antibodies present in the control animals, the antibodies present in the serum and saliva of all animals were subjected to the quantitative agglutination test using the conventional micro-titre method. Also, the adherence inhibition test was effected in conventional manner.

(a) The vaccines (antigens) used for the agglutination test were prepared in the following manner:

$Streptocccus$ $mutans$ Mutant Strain K-Dp (FERM BP 317), $S.$ $mutans$ KH2 (FERM BP 366) and various other Human type strains of S. mutans such as $S.$ $mutans$ NCTC 10449 (serotype "c"), OMZ176 (serotype "d"), P-4 (serotype "e"), OMZ175 (serotype "f") and K1R (serotype "g"), all being well-recognized reference strains of $S.$ $mutans$ found in the oral cavity of humans, were respectively cultured for 24 hours using Tryptocase Soy Broth (pH 7.8; each 15 ml; commercially available from BBL., U.S.A.) containing 0.5 % of yeast extract. On each occasion, after completion of culturing, the cultured broth was centrifuged (8000 r.p.m./20 min) to separate the cells. The cells were suspended in a 0.75M phosphatebuffered 1M sodium chloride solution (pH 7.0; 100 ml) containing 0.2 mM glutaraldehyde. The cell suspension was allowed to stand at 37° C. for 12 hours. Then the cells were recovered by centrifugation (8000 r.p.m./20 min) and suspended in a similar solution of sodium chloride (pH 7.0) at a concentration of an optical density of 0.50 at 550 nm to obtain an antigen solution.

The saliva or serum collected from each animal was diluted to give a 10-fold greater amount and further diluted (X 2) using a similar buffer solution. On each occasion, the diluted serum or saliva (0.025 ml) was mixed with an equal amount of the antigen solution by using a micro-titre plate. The mixture was allowed to stand at 37° C. for 4 hours to allow the reaction to take place. Before evaluation the unaided eye, the reaction mixture was left at 5° C. overnight.

(b) For determining the adherence-inhibiting ability, the serum or saliva collected from each animal was diluted with TYC medium (pH 7.2; Stoppellar et al., Archs. Oral Biol., 12, 1199-1201, 1967) to give a 10-fold greater amount. The mixture was filtered under sterilized conditions by using a membrane filter (0.45 micron; commercially product of Milipore Corpn., U.S.A.) and subjected to multiple dilution (X 2) using the same medium. Separately, the above-mentioned strains of S. mutans K-Dp (FERM BP 317), KH2 (FERM BP 366) and various other reference strains of Human type S. mutans were cultured respectively for 24 hours using Todd Hewit Broth (pH 7.8; each 10 ml; BBL., U.S.A.). On each occasion, one platinum loop of the cultured broth was transferred to the diluted serum or saliva solution (3 ml). The mixture was incubated at 37° C. for 24 hours. The cultured liquor was removed from the test tube by washing with water. The cells adhered to the tube wall were dyed with a methylene blue solution to evaluate the adherence.

(4) In the experiments, a reference vaccine, as described hereinafter, was also studied. The results are shown in the tables hereinafter, which may be summarized as follows:

(a) There is a significant difference between the dental caries induction ratio of the immunized animals and the corresponding ratio of the control (untreated) animals. Where the animals immunized with vaccines I and/or II (PLS antigens I and/or II) were challenged with the strains of S. mutans K-Dp (FERM BP 317) and KH2 (FERM BP 366) respectively, the animals immunized with PLS antigen I and challenged with K-Dp strain exhibited a higher dental caries induction ratio, as shown in the following Table 2. However, where the animals were immunized with both PLS antigens I and II and challenged with K-Dp and KH2 strains independently, no significant difference was noted between the dental caries induction ratios of the two groups, as shown in the following Table 3.(5) No significant difference was observed between the dental caries induction of the control (untreated) animals and that of the animals immunized with a reference vaccine (hereinafter described). By investigating the antibodies present in the serum or saliva of each animal, it has been noted that, even when agglutinin was produced by the action of the vaccines of the present invention, its amount was relatively small, whilst antibodies capable of inhibiting the adherence were present in the saliva in some cases.

(b) In the serums of the animals immunized with the reference vaccine, the presence of agglutinin and the absence of antibodies capable of inhibiting the adherence were noted.

(c) With respect to the fact that the whole cells were used for the preparation of the reference vaccine, it cannot be said that at least a small amount of any antigen originating from the pili-like structures may not be present in the reference vaccine. However, its effect is insignificant.

(6) A second reference vaccine was prepared in a similar manner to that described hereinafter with the exception that 0.5% phenol was used instead of formalin for inactivation. The results from this second reference vaccine was significantly inferior to the results from the first reference vaccine.

(7) The results obtained by using various other Human type strains of S. mutans than K-Dp and KH2 are not shown in the following tables because of the quantative identity with the results shown herein.

(8) A further reference vaccine was prepared in the following manner with reference to Example 1 of British Patent No. 1,375,866 which discloses a vaccine comprising as antigen the whole cells of Streptococcus mutans SSC having the same characteristics as the characteristics of S. mutans NCTC 10449, a well-recognized representative cariogenic strain (serotype "c") in the oral cavity of humans (cf. page 5, lines 2-9 of the reference patent).

S. mutans NCTC 10449 was cultured at 37° C. for 24 hours by using a flat layer of bactobrain heart infusion broth (commercially available from Difco., U.S.A.) with 2% agar added. The harvested cells were suspended in a sterile saline solution (0.85% w/v NaCl; 100 ml) and washed 3 times with a saline solution (0.68% NaCl; each 100 ml) by centrifugation (each 8000 r.p.m/20 min. for each).

The cells were suspended in a sterile saline solution (0.85% w/v; 200 ml) containing 0.6% formalin and incubated overnight at room temperature to kill the cells. The inactivated cells were washed three times with a sterile saline solution (0.68% w/v; each 100 ml) by centrifugation (each 8000 r.p.m./20 min) and suspended in a similar sterile saline solution (0.68% w/v; 10 ml). The stock bacteria were checked for sterility by inoculation of 0.1 ml portion in each of 10 tubes of BBL fluid thioglycolate medium and incubated at 37° C. for 10 days. Methiolate (0.1% solution of thimerosal in alcohol) was added as a preservative to the sterile stock at a final concentration of 1:10,000. The remaining suspension was homogenized by treating with ultrasonic waves (20 KHz/10 min) and diluted with a saline solution (0.68% w/v) containing 0.01% thimerosal to give a final concentration of about $2 \times 10^6$ cells/ml to obtain the desired vaccine.

TABLE 1

| Group | 1 | 2 | 3 |
|---|---|---|---|
| Immunizing antigen | Antigen I | Untreated control | Reference vaccine |
| Challenge strain** | K-Dp | K-Dp | K-Dp |
| Body weight increase (g) | 95.5 | 67.5 | 91 |
| Infection ratio (%) | 30 | 100 | 90 |
| Dental caries induction ratio (%) | 7.5 | 68.3 | 59.2 |
| Antibody titre | | | |
| Agglutinin A | <4–4 | <4 | 16–32 |
| Agglutinin B | <4 | <4 | <4–4 |
| Adherence inhibition | | | |
| A | — | <10 | <10 |
| B | 40 | <10 | <10 |

[Notes:
A ... in the serum; B ... in the saliva.
Infection ratio ... all hamsters = 100%;
Dental caries induction ratio ... all molars = 100%.
The indicates figures are the mean values of all animals in each group.]
**FERM-BP 317.

TABLE 2

| Group | 1 | 2 | 3 | 4 | 5 | 6 |
|---|---|---|---|---|---|---|
| Immunizing antigen | I | I | II | II | (Untreated) | |
| Challenge strain | K-Dp* | KH2** | K-DP | KH2 | K-DP | KH2 |
| Body weight increase (g) | 86 | 89 | 88 | 91 | 90 | 86 |
| Infection ratio (%) | 10 | 20 | 40 | 10 | 100 | 100 |
| Dental caries induction ratio (%) | 11 | 4.2 | 22.5 | 0.8 | 70 | 51.8 |
| Antibody titre | | | | | | |

TABLE 2-continued

| Group | 1 | 2 | 3 | 4 | 5 | 6 |
|---|---|---|---|---|---|---|
| Agglutinin A | <4 | <4 | <4 | <4 | <4 | <4 |
| Agglutinin B | — | — | — | — | — | — |
| Adherence inhibition | | | | | | |
| A | — | — | — | — | — | — |
| B | — | — | — | — | — | — |

[Notes:
cf. Table 1. I ... antigen I; II ... antigen II]
*FERM-BP 317; **FERM-BP 366.

TABLE 3

| Group | 1 | 2 | 3 | 4 |
|---|---|---|---|---|
| Immunizing antigen | (I + II) | | (Untreated) | |
| Challenge strain | K-Dp* | KH2** | K-Dp | KH2 |
| Body weight increase (g) | 82 | 80 | 84 | 79 |
| Infection ratio (%) | 20 | 10 | 100 | 100 |
| Dental caries induction ratio (%) | 4.2 | 1.7 | 60.8 | 34.2 |
| Antibody titre | | | | |
| Agglutinin A | <4 | <4 | <4 | <4 |
| Agglutinin B | <4 | <4 | <4 | <4 |
| Adherence inhibition | | | | |
| A | <10 | <10 | <10 | <10 |
| B | 20 | 20 | <10 | <10 |

[Notes:
cf. Table 1. I + II ... Mixed vaccine]
*FERM-BP 317; **FERM-BP 366

Experiment 2

Antibodies:

Among hamsters (21 days after birth) used as test animals, the first and second groups were test groups and the third and fourth groups were used for control groups. *Streptococcus mutans* Mutant Strain K-Dp (FERM BP 317) and *S. mutans* Strain KH2 (FERM BP 366) were respectively cultured for 24 hours at a pH of 7.5-7.8 by using Tryptocase Soy Broth (commercial product of BBL., U.S.A.).

Cultured broth containing about $10^8$ living cells of KDp strain per ml was orally administered to each animal of the first and third groups at a dose of 0.1 ml once daily and continued for 5 days.

Similarly, KH2 strain was administered to each animal of the third and fourth groups. The adherence of the strains of *S. mutans* to the teeth of all the animals was confirmed. Then, a dental paste prepared by the method of Example 10 (0.1 g per animal; containing 2 units of PLS antigen I antibodies and 2 units of PLS antigen II antibodies) was applied to the molar surfaces of each animal of the first and second groups by means of a small brush. The application was continued once daily for 14 days.

During the test period of 60 days, samples were collected after various periods from the molar surfaces of each animal. Each sample was cultured for 72 hours using TYC agar plate medium (15 ml; Stoppelaar et al) and Mitis-salivarius agar medium (15 ml; commercial product of Difco., U.S.A.) in order to investigate the adherence of *S. mutans*. It was observed that the concentration of *S. mutans* in the oral cavity of each animal of the first and third groups gradually decreased by administration of the antibodies. Strains of *S. mutans* disappeared from a proportion of the animals after about 2-4 weeks and from the remaining animals after about 4-7 weeks. No decrease of the concentration of *S. mutans* in the oral cavity of any animal of the control groups was found. After completion of the test, each animal was anesthetized by injection of pentabarbital and the maxilla was collected from each animal. The soft part of the maxilla was removed by treating at 120-125° C. for 1-2 minutes in an autoclave. The maxilla was washed with water and dried to prepare a sample of the teeth. All molars of each animal were examined to determine the ratio of infection (adherence) with *S. mutans* and the ratio of induction of dental caries with reference to the number of various teeth. The results are indicated in the following Table 4.

TABLE 4

| Group | Antibodies used | Serotype of S. mutans | A | B | C |
|---|---|---|---|---|---|
| 1 | I and II | c | 77.2 | 20 | 7.5 |
| 2 | I and II | d | 74.2 | 0 | 0 |
| 3 | untreated | c | 77.4 | 90 | 65 |
| 4 | untreated | d | 74.0 | 70 | 34.2 |

Notes:
A ... increase of body weight (average %); body weight before the beginning of administration = 100%.
B ... infection ratio (all molars = 100%)
C ... carious ratio (all molars = 100%)

Experiment 3

Antibodies:

The change in the concentration of the strains of *S. mutans* in the oral cavity of humans resulting from the use of the dental paste described in Example 10 (containing PLS antigen I antibodies and PLS antigen II antibodies at an equal titre of 4 units) was tested. The test panel consisted of 10 adults (5 men and 5 women). From the oral cavity of each adult, dental plaque was collected three times, and the samples were cultured in a similar manner to that described in Experiment 1. Moreover, the formation of dental plaque and cysts in the oral cavity was investigated as set out in "The guide line of the procedure of smearing fluoride" issued by The Ministry of Welfare and Health of The Japanese Government. As a result, the existence of strains of *S. mutans* in all the adults was confirmed. Every day after breakfast and dinner, the dental paste was applied by all members of the test group to their teeth. The method of application was not specified. At least once per week, dental plaque was collected from the oral cavity of each member and cultured in a similar manner to that described above in order to investigate the change in the concentration of the strains of *S. mutans* in the oral flora. All or almost all strains of S. mutans disappeared from 3 members after about 2-3 weeks and from the remaining members after about 4-7 weeks. The OHI values of all members, which were determined by using erythrosine, decreased significantly over the test period.

Experiment 4

Antibodies:

A buccal prepared by the method of Example 8 (containing PLS antigen I antibodies and PLS antigen II antibodies at an equal titre of 3 units) was orally administered to each member of a test group consisting of 20 women (adults) and the change in concentration of *Streptococcus mutans* in their oral cavities were investigated. 19 women were the hosts of *S. mutans* of serotype "c" and one woman only was the host of *S. mutans* of serotype "d".

Every day at bed time, a buccal was administered orally to each member of the test group. The buccal was kept in the oral cavity for as long as possible. About 2 weeks after the beginning of administration, no *S. mutans* was could be isolated from 5 members of the test group. The concentration of *S. mutans* in the oral flora of the remaining members decreased gradually so that about 4 weeks after the beginning of administration, the concentration of *S. mutans* in their oral cavities was very low. The OHI values of all members decreased greatly over the test period.

It was noted that the inhibiting effect resulting from the administration of buccals was at least equal or superior to the effect of dental paste, as the stay time of a buccals in the oral cavity is longer than the stay time of usual dentifrices.

We claim:

1. A non-cariogenic composition for inhibiting human dental caries induced by Streptococcus mutans which comprises as active ingredient at least one antibody selected from a group consisting of two antibodies in association with a pharmaceutically acceptable carrier or excipient, said antibody being prepared by the steps of immunizing a mammal with an effective amount of at least one antigen selected from the group consisting of PLS-I and PLS-II antigens isolated from the fimbriae on the cell surface of mutant strains of *S. mutans* K-Dp (Ferm-BP No. 317) or KH2 (Ferm-BP No. 366) said isolation step being effected at a temperature at which denaturation of said antigens is substantially avoided and then recovering the resulting antibodies from said mammal.

2. A non-cariogenic composition for inhibiting human dental caries induced by *Streptococcus mutans* which comprises as active ingredient at least one antibody in association with a pharmaceutically acceptable carrier or excipient, said antibody being prepared by the steps of immunizing a mammal with an effective amount of at least one PLS antigen isolated from the fimbriae of strains of *S. mutans*, said isolation step being effected at a temperature at which denaturation of said antigen is substantially avoided, and then recovering the resulting antibodies from said mammal.

3. A non-cariogenic composition for inhibiting human dental caries induced by *Streptococcus mutans* which comprises as active ingredient at least one antibody in association with a pharmaceutically acceptable carrier or excipient, said antibody being prepared by the steps of immunizing a mammal with an effective amount of at least one antigen isolated from the fimbriae of strains of *S. mutans* bearing serotypes c, d, e, f and g, said isolation step being effected at a temperature at which denaturation of said antigens is substantially avoided, and then recovering the resulting antibodies from said mammal.

4. The non-cariogenic composition of claim 3, wherein said at least one antigen is selected from a group consisting of first and second antigens, said first antigen being isolated from the fimbriae of a strain of *S. mutans* bearing serotypes c, e, f, or g and said second antigen being isolated from the fimbriae of a strain of *S. mutans* bearing serotype d.

5. A composition as claimed in claim 1 in a form suitable for oral administration.

6. A composition as claimed in claim 5 in the form of chewing gums, candies, ice-creams, syrups, juices and drinks containing lactic acid-producing living bacilli.

7. A composition as claimed in claim 5 in the form of dentifrices, gargles and pastes.

8. A composition as claimed in claim 5 in a form selected from buccals and troches.

* * * * *